United States Patent [19]

Bradshaw et al.

[11] Patent Number: 4,946,459
[45] Date of Patent: Aug. 7, 1990

[54] INTRAMEDULLARY DEVICE

[75] Inventors: Anthony J. Bradshaw, Suwanee; Raymond T. Morrissy, Atlanta; Christopher J. Ketchum, Doraville; John R. Hawkins, Warm Springs, all of Ga.

[73] Assignee: Georgia Tech Research Corporation, Atlanta, Ga.

[21] Appl. No.: 445,376

[22] Filed: Dec. 4, 1989

[51] Int. Cl.$^5$ .............................................. A61F 5/04
[52] U.S. Cl. ...................................... 606/62; 606/63; 606/64
[58] Field of Search ................... 606/62, 63, 64, 65, 606/66, 67, 68

[56] References Cited

U.S. PATENT DOCUMENTS

| | | | |
|---|---|---|---|
| 3,760,802 | 9/1973 | Fischer et al. | 606/63 |
| 3,779,239 | 12/1973 | Fischer et al. | 606/63 |
| 3,977,398 | 8/1976 | Burstein | 606/62 |
| 3,986,504 | 10/1976 | Avila | 606/63 |
| 4,016,874 | 4/1977 | Maffei et al. | 606/62 |
| 4,091,806 | 5/1978 | Aginsky | 606/63 |
| 4,262,665 | 4/1981 | Roalstad et al. | 606/62 |
| 4,275,717 | 6/1981 | Bolesky | 606/63 |
| 4,453,539 | 6/1984 | Raftopoulos et al. | 606/63 |
| 4,697,585 | 10/1987 | Williams | 606/64 |

Primary Examiner—Mickey Yu
Assistant Examiner—Charles H. Sam
Attorney, Agent, or Firm—Thomas & Kennedy

[57] ABSTRACT

An intramedullary device for fixing and extending separated portions of a long bone within the body of a patient has a nail member within and affixed to one portion of the bone and an adjustment assembly within and affixed to a separate portion of the bone. The adjustment assembly has a moveable member which bears against an end of the nail and can be moved from outside the patient to adjust the separation between the portions of the bone.

23 Claims, 2 Drawing Sheets

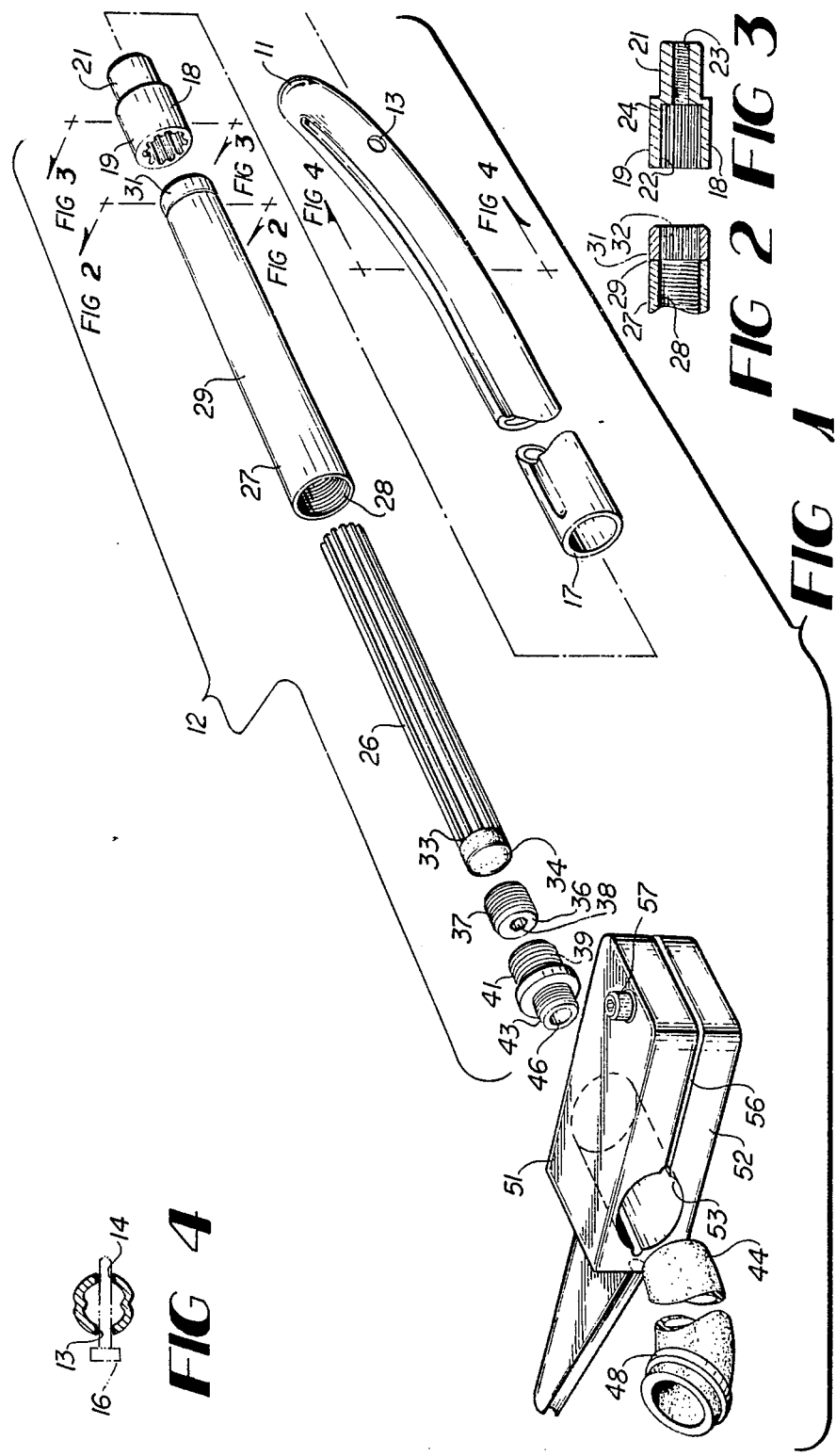

INTRAMEDULLARY DEVICE

FIELD OF THE INVENTION

This invention relates to surgical devices and, more particularly, to an intramedullary extension, compression and fixation device for use in the treatment of long bones of the body.

BACKGROUND OF THE INVENTION

When one of the long bones of the body, such as the femur, is fractured, treatment of the fractured bone requires that the parts of the bone at the fracture site be substantially immobilized in abutting relationship during the knitting process. Any longitudinal, transverse, or rotational movement of one section of bone relative to the other delays the healing process, and can completely undo the progress of the reuniting of the bone sections. In general, two different approaches have been used to accomplish the desired ends of immobilization and longitudinal compression sufficient to maintain the bone sections in contact.

One approach involves driving metallic pins through the two sections of bone to be joined, and connecting them to one or more plate members bearing against the bone sections externally thereof, as shown in U.S. Pat. No. 4,776,330 of Chapman et al. Such an arrangement injures the flesh and muscle surrounding the bone, and the multiplicity of pins driven through the bone tend to weaken its hard outer layer. Plates also tend to stress-shield the bone and it does not become strong underneath the plates, and plates are not always able to bear sufficient stress for many applications. Equally as important is the necessity of subjecting the patient to two major operations, one to install the plates and pins, and one to remove them after healing. Any invasion of the body gives rise to the possibility of infection, therefore such invasions should be minimized if at all possible.

A second approach to treating problems of the femur, for example, involves the use of an intramedullary nail which is inserted into the bone channel and affixed therein by any of a number of ways. Intramedullary fixation is advantageous because it allows the femur, for example, to bear full weight and undergo normal stimulation for growth and renewal. One such arrangement is shown in U.S. Pat. No. 3,717,146 of Halloran. wherein a threaded, slotted nail is driven into the medullary canal of the femur, with the threads on the exterior of the nail engaging the interior walls of both sections of bone to align them and pull them together in compression. After healing of the bone at the break the nail may be removed through a hole drilled in the upper or proximal end of the femur. For additional strengthening, a compression plate may be used at the fracture site.

U.S. Pat. No. 4,091,807 of Aginsky discloses a split nail which is inserted in the medullary canal and one end portion of the nail is expanded by a screw actuated expansion wedge to grip the inner wall of one section of the fractured femur. The other end of the nail is anchored to the proximal end of the femur, and continued rotation of the wedge actuating screw pulls the two sections of the femur together in compression and in alignment. The nail is removed after the bone is healed. Another example of a removable intramedullary nail is shown in U.S. Pat. No. 4,805,607 of Engelhardt et al.

Some arrangements dispense with the intramedullary nail approach and utilize instead members inserted into each bone section and anchored thereto, and a central alignment pin which is slidable, but not rotatable, in the members in each bone section. These arrangements are all designed to remain permanently within the medullary channel. Typical of such arrangements are those shown in U.S. Pat. Nos. 4,467,794 of Maffei, 4,016,874 of Maffei et al and 4,262,665 of Roalstad.

Among the advantages of the nail arrangement are the necessity, usually, for only one incision in the patient's buttock, for example, while the fracture is being reduced and the nail passed through the bone sections, and the relatively easy removal of the nail after the healing process is completed. On the other hand, the nails as such do not prevent rotation of the bone sections relative to each other, which can be as damaging as sudden tension applied to the break area. One remedy for this problem is the use of a cross nail as shown in U.S. Pat. No. 4,697,585 of Williams. The cross nail is mounted in a slot cut in the neck and head of the proximal end of the femur and has a bore through which the intramedullary nail passes. A suitable set screw arrangement firmly joins the cross nail to the intramedullary nail so that there can be no rotation therebetween, and the distal end of the intramedullary nail is fixed in position by pins extending through the bone and the nail. With such an arrangement, rotation of the bone sections relative to each other is prevented. A variation of the cross nail arrangement is shown in the aforementioned Chapman et al patent.

In all of the foregoing arrangements, trauma centers must keep an inventory of incremental nail lengths so that a random, diverse incoming patient population may be accommodated. In those cases where permanent bone inserts are to be used, a premium is placed upon a close estimate of the patients correct bone length since, once installed, the apparatus is not adjustable, nor is it easily replaced. Intramedullary nails of differing lengths can be substituted for those in place, however, at least at the early stages of the bone healing, the fracture must be reduced again, necessitating a second operation on the patient.

In some cases, as in congenital abnormalities, it is desirable to lengthen the femur of the patient, or to correct leg length discrepancies. Leg or femur lengthening procedures include an external "halo" brace surrounding the leg, with crossed pins driven through the flesh and the bone on either side of a bone separation, and external screws extending between proximal and distal braces. Such an arrangement is both cumbersome and difficult to install, and limits the patient's movements and can cause continuing damage to flesh and muscle. Because the pins remain penetrating the flesh and skin, infection is a constant danger. Another common method for relatively short lengthening of the femur, for example, is bone grafting, which is a painful process and requires invasion surgery for each graft.

In none of the foregoing prior art arrangements is provision made for adjusting the lengths of the intramedullary device after insertion, thus the proper length of the bone after reduction of the fracture can only be estimated, and an intramedullary device of an estimated proper length inserted. In addition, bone lengthening can only be accomplished with an externally adjustable device, or by means of a grafting operation, or by completely replacing the nail.

SUMMARY OF THE INVENTION

The present invention is an intramedullary device which, unlike prior art devices, can be adjusted in length after installation to provide a "fine tuning" of the bone length on a continuing basis during the bone mending process, and which can also be used in a bone lengthening procedure to correct abnormalities in bone length, such as congenital abnormalities.

In a preferred embodiment the intramedullary device of the invention comprises, as assembled, a slotted nail member which extends toward the distal end of the bone, and is affixed at the distal end by means of pins or screws extending through the bone. At the proximal end of the nail is an interiorly splined receptacle preferably affixed to the end of the nail as by welding. The splined receptacle has an interior shoulder therein approximately mid-way of its length.

An exteriorly splined adjustment shaft is adapted to fit into the splined receptacle and to bear against the shoulder thereof. The shaft is mopunted within an elongated cylinder having an interiorly splined end cap at its distal end whereby the shaft is free to slide within the cylinder but is restrained from rotation with respect thereto. The interior of the cylinder is threaded over a major portion of its length from the proximal end toward the splined end cap. The proximal end of the shaft has a stop collar mounted thereon to prevent the shaft from sliding out of the cylinder through the end cap, but to permit insertion and removal of the shaft through the proximal end of the cylinder. An adjustment screw is threaded into the threaded cylinder and is adapted to bear against the stop collar. The screw has a socket, such as a hexagonal Allen socket, in its proximal end to permit driving the screw into the cylinder, and hence driving the splined shaft toward the distal end of the bone, which in turn drives the nail toward the distal end away from the cylinder. A cylindrical end cap having external threads thereon is threaded into the cylinder after the adjusting screw has been inserted therein. Mounted to the end cap extending therefrom is a longitudinal section of biocompatible tubing.

In order that the foregoing assembly be prevented from rotating relative to the bone sections, a cross nail having a bore through which the cylinder extends is provided and is adapted to be firmly fixed to the cylinder by means of a suitable set screw.

The intramedullary nail and adjusting assembly is applied to the patient by the steps of cutting a slot in the neck and head of the femur, for example, sufficient for the cross nail to be seated therein; passing the nail and adjusting assembly through an incision in the patient's buttock, for example, through a hole bored at the top of the bone and through the bore in the cross nail into the medullary canal or channel; reducing the fracture by passing the nail therethrough, which sometimes requires an incision at the site of the fracture; passing the nail into the distal section of bone and anchoring it thereto; and tightening the set screw on the cross nail to affix it to the cylinder of the adjusting mechanism. An elongated wrench may then be passed through the tubing and the end cap into the head of the adjusting screw, which is then rotated to move the splined shaft and nail to adjust the assembly to the desired length. Whenever further length adjustments are called for, it is only necessary to reopen the small incision in the patient's buttock sufficient to allow insertion of the wrench through the tubing to the adjusting screw.

The procedure for lengthening the femur, for example, is the same, except that the bone is deliberately parted, and the two resulting sections are forced apart by lengthening the assembly. During the bone mending process, further length adjustments can be made as desired. Thus incremental increases in length can be made periodically, allowing time for adaptation of the tissues between each incremental increase.

In cases where it is determined that the length is too great, the adjusting screw can be backed off and the normal compressive forces of the patient's muscles will act to shorten the nail assembly.

When the bone mending process is completed, or at least sufficiently advanced to where lengthening and immobilization are no longer necessary, the entire nail assembly may be removed from the patient through the incision in the patient's buttock, and the cross nail removed through a second small incision. Thus repetitive large invasions of the patient's body are not necessary, damage to the patient's flesh and muscle is minimized, a large inventory of nails of varying lengths is not necessary, and proper bone length is achieved to a greater degree of accuracy than has been possible heretofore.

The various features and advantages of the present invention will be more readily apparent from the following detailed description, read in conjunction with the accompanying drawings.

BRIEF DESCRIPTION OF THE DRAWINGS

FIG. 1 is an exploded, perspective view of the intramedullary nail and adjusting assembly of the present invention;

FIG. 2 is cross-sectional view along the lines I—I of FIG. 1;

FIG. 3 is a cross-sectional view along the lines II—II of FIG. 1;

FIG. 4 is a cross-sectional view along the line III—III of FIG. 1;

DETAILED DESCRIPTION

Figure 5:
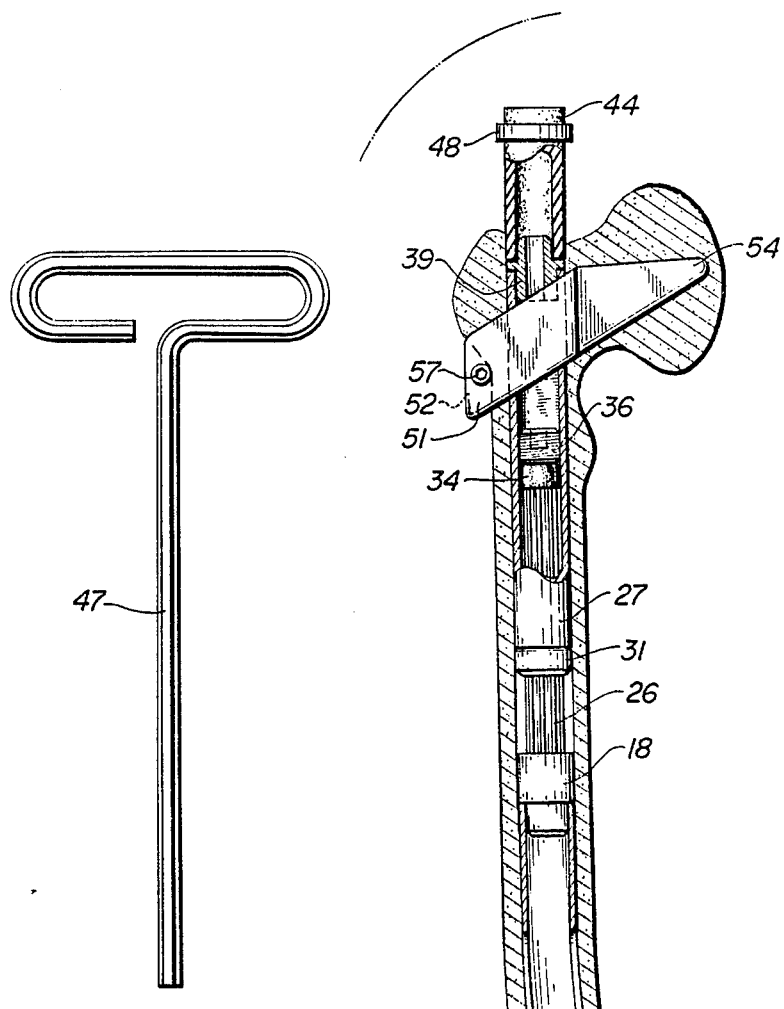
FIG. 5 is a plan view of an adjusting wrench for use with the apparatus of FIG. 1.

In FIG. 1, there is shown a preferred embodiment of the device of the present invention which comprises an intramedullary nail 11 and adjustment assembly 12 therefor.

Nail 11 preferably has a longitudinally extending slot, not shown in the wall thereof, and preferably has a quatrefoil cross-section, as best seen in FIG. 4. Also shown in FIG. 4 is a bore 14 in the wall of the nail opposite a bore 13 through which a threaded fastening pin 16, shown in dashed outline, is passed for pinning the nail 11 to the femur. As more readily seen in FIG. 6, the bore 13 and the bore 14 are adjacent the distal end of the nail, and if necessary, additional bores 14 and pins 16 may be used. As can be seen in FIG. 1, nail 11 is curved to match, at least approximately, the natural curvature of the femur, for example, and the slot and quatrefoil shape impart a small degree of flexibility to the nail 11 to permit it to follow a medullary canal bend in the bone being treated. Nail 11 can be made of any suitable nontoxic, non-degenerating material such as, for example, stainless steel or a titanium base alloy, capable of withstanding the stresses to which it is subjected without deformation. Inserted in the proximal end 17 of nail 11 and affixed thereto as by welding, is a stepped cylindrical receptacle 18 having a first section 19 of approximately the external diameter of nail 11 and a second section 21 having a diameter approximating the inner diameter of nail 11. Section 19 has a splined bore 22 therein, and section 21 has a threaded bore 23 of lesser diameter, thereby forming a shoulder 24 approximately midway of the length of receptacle 18.

A splined adjustment shaft 26 is adapted to slide within bore 22 and bear against shoulder 24, as will be discussed more fully hereinafter. Shaft 26 is slideably carried within an elongated hollow cylinder 27 which has threads 28 extending the length of the interior thereof. Affixed to the distal end 29 of cylinder 27 as by welding or threading is a cylinder end cap 31 having a splined bore 32 within which spline shaft 26 is adapted to slide. Thus splined shaft 26 can move longitudinally relative to nail 11 and cylinder 27, but it is restrained from rotating relative thereto, and it, in turn prevents relative rotation between cylinder 27 and nail 11. At the proximal end 33 of shaft 26 is a stop collar 34 affixed to the shaft. Collar 34 may be of plastic or any other suitable material, and has a diameter such that it can pass freely through cylinder 27, but cannot pass through end cap 31, being prevented from doing so by the lands of the splines therein. Thus shaft 26 cannot pass out of the distal end of cylinder 27.

An adjustment screw 36 having external threads 37 extending its entire length is adapted to mate with the threads 28 in cylinder 27 and to bear against stop collar 34. Thus rotation of screw 36 is converted into translational movement of shaft 26. The head or proximal end of screw 36 has a wrench socket 38 therein, such as a hexagonal Allen wrench socket for rotating screw 36 and hence imparting longitudinal movement to shaft 26. A cylinder top cap 39 has a first externally threaded portion 41 adapted to be screwed into cylinder 27, a collar 42, and a second externally threaded portion 43 onto which is threaded a length of bio-compatible tubing 44. Cap 39 has a bore 46 extending therethrough of sufficient diameter to permit free passage of an adjusting wrench, such as wrench 47 shown in FIG. 5, for adjustment screw 37. Bio-compatible tubing 44 is preferably flexible and is made of an inert plastic which will not deteriorate while in the patient's body, nor will it have any toxic effect on the patient. The tubing may be cut to any desired length, depending upon the size of the patient and is of an internal diameter such that it can be screwed onto portion 43 of top cap 39 to affix it thereto. If desired, a hose clamp or other suitable means may be used to clamp the end of tube 44 firmly to portion 43. The proximal end of tube 44 has a metallic ring 48 affixed thereto. Ring 48 serves two functions. Inasmuch as the entire assembly is within the patient's body and where access to the tube 44 is necessary, the ring 48 makes it possible to detect the location of the proximal end of tube 44 fluoroscopically. In addition, ring 48 prevents the end of tube 44 from being deformed or closed by the patient's muscles or flesh, thus insuring an opening for free passage of the adjustment wrench 47.

When the nail 11 and adjustment assembly 12 are inserted in the patient, it is necessary for proper operation that assembly 12 be both rotationally and longitudinally fixed with respect to the bone, such as the femur. When the assembly 12 is rotationally fixed, the splined shaft 26 also rotationally fixes the nail 11 while permitting it to be moved longitudinally relative to assembly 12. It is to be understood that while shaft 26 is shown as splined, other arrangements could be used to prevent rotation of the shaft 26, such as, for example, a single keyway, a flat surface or shaft 26 or an elliptically or irregularly shaped shaft cross-section. In order that assembly 12 be thus fixed within the bone, a cross-nail 51 is provided. Nail 51 comprises a block portion 52 having an angled bore 53 extending therethrough for receiving cylinder 27 and a blade portion 54. Block portion 52 is bifurcated by means of a slot 56 cut therein extending from the end of block portion 52 to the bore 53. A set screw 57 is provided to draw the bifurcated portions of block 52 together, thereby firmly clamping cross nail 51 to sleeve 27 and preventing movement therebetween.

Figure 6:
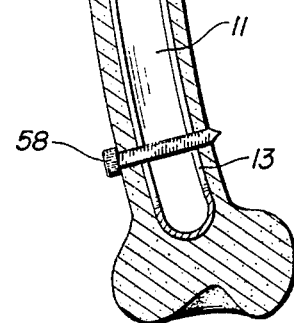
FIG. 6 is a view of the nail and adjusting apparatus as assembled and inserted into a femur.

In FIG. 6, the intramedullary device of the invention is shown as installed in a femur. In the arrangement shown, the device installation is for femur lengthening, and the bone is deliberately separated at point A, however, the installation would be the same for a fractured femur. Deliberate separation of the bone does not necessarily entail total separation, since it is advantageous to leave the periosteal tissues intact. The hard outer portion of the bone can be cut or separated with an intramedullary bone saw. Cross nail assembly 51 is inserted and seated in a notch or channel (shown in dashed lines) cut into the neck or head of the femur. While set screw 57 is shown as being within the confines of the channel, the length of block 52 can be made such that set screw 57 is completely outside the bone, thereby facilitating access thereto.

An opening is made in the patient's buttock (shown in dashed lines) and nail 11 is inserted therethrough, through a passageway drilled in the top of the femur and through the bore 53 in cross nail 51 into the medullary canal, pushed or driven down into the lower portion of the separated bone, and pinned adjacent the distal end, as at point B. The adjustment assembly is then likewise inserted through the opening, the top of the femur, the bore 53 in cross nail 51, and into the medullary canal until the splines on shaft 26 mesh with the splines in receptacle 18 and the end of shaft 26 abuts shoulder 24. Set screw 57 is then tightened to clamp cross nail 51 firmly to sleeve 27.

As thus far described, cross nail 51 anchors adjustment assembly 12 both rotationally and longitudinally, and, inasmuch as shaft 26 only moves longitudinally nail 11 has no rotational forces applied thereto, and both sections of the bone are prevented from rotating relative to each other. When adjusting wrench 47 is inserted through the tube 44 and cylinder top cap 39 into the socket in the end of adjustment screw 36 and rotated to drive screw 36 further into cylinder 27, shaft 26 is driven longitudinally, and thereby moves nail 11 and the lower section of bone longitudinally thus increasing the bone separation at point A. As a soft callous forms between the two bone sections at point A, screw 36 is rotated in increments over a period of time, thus incrementally increasing the separation at point A, with the end result that, after the callous hardens, a lengthened femur is achieved. It is only necessary at most to invade the patient's body in any major way once, and that is in some instances, when the bone is severed. Insertion and removal of pins 58 requires only a small opening, as does insertion and removal of the entire assembly. Forming the notch in the neck and head of the femur does require a major opening, but removal of cross nail 51 does not, and tightening of screw 57 can be made through a small stab opening. Most importantly, once the device of the invention is installed, subsequent adjustment thereof requires only a single small stab opening or wound in the patient's buttock, and, after healing, only small wounds are necessary to remove the entire assembly, since the device, with the exception of pins 58 and cross nail 51 is removable through the opening in the buttock. Once adjustment assembly 12 has been removed, an elongated rod having threads on its end which match the threads of threaded bore 23 in receptacle 18 can be inserted into the opening and screwed into the bore 23, and nail 11 can then be pulled out through the opening in the patient's buttock.

From the foregoing it can be seen that the device of the present invention constitutes an apparatus for adjusting the length of the long bone internally of the patient's body while immobilizing the sections of the separated or fractured bone. The use of external devices for adjusting the length of the bone is not necessary, and multiple operations on the patient are avoided, while adjustment of the bone length is achieved with a degree of precision not heretofore possible.

While the invention has been shown in a preferred embodiment thereof, numerous changes or modifications may occur to workers in the art without departure from the spirit and scope of the invention.

We claim:

1. An intramedullary fixation device for fixing a long bone separated into upper and lower sections, the bone having a proximal end and a distal end, said device comprising, in combination,
    a nail member having proximal and distal ends and adapted to be inserted through a hole drilled in the proximal end of the bone and to extend toward the distal end of the lower section of the bone,
    means for attaching said distal end of the said nail member to the lower section of the bone adjacent the distal end thereof,
    a receptacle affixed to the proximal end of said nail member,
    an adjustment shaft having one end thereof adapted to fit within and bear against said receptacle,
    a hollow cylinder member having proximal and distal ends and adapted to contain said adjustment shaft, said cylinder member being adapted to be inserted into the bone through the hole in the proximal end thereof,
    means for preventing rotational movement of said adjustment shaft relative to said receptacle and to said cylinder member while permitting longitudinal movement therebetween,
    an adjustment member for imparting longitudinal movement to said adjustment shaft relative to said cylinder member,
    and fixation means for rotationally and longitudinally fixing said cylinder member adjacent the proximal end of the bone.

2. An intramedullary fixation device as claimed in claim 1 wherein said receptacle has a first bore extending partially therethrough and a second, smaller diameter bore forming a shoulder within said receptacle against which said one end of said adjustment shaft is adapted to bear.

3. An intramedullary fixation device as claimed in claim 2 wherein said means for preventing rotational movement of said adjustment shaft comprises external splines on said shaft extending longitudinally thereof, and matching internal splines in said cylinder member and said first bore of said receptacle.

4. An intramedullary fixation device as claimed in claim 1 and further including stop means affixed to the end of said adjustment shaft remote from said one end.

5. An intramedullary fixation device as claimed in claim 1 wherein the interior of said hollow cylinder member is threaded for substantially the entire length thereof.

6. An intramedullary fixation device as claimed in claim 5 wherein said adjustment member comprises a threaded screw having proximal and distal ends and adapted to be threaded into the interior of said hollow cylinder member.

7. An intramedullary fixation device as claimed in claim 6 wherein said adjustment member has a socket in the proximal end thereof adapted to receive an adjusting wrench.

8. An intramedullary fixation device as claimed in claim 5 and further including a threaded cylinder top cap having a bore extending therethrough and adapted to be screwed into the proximal end of said hollow cylinder member.

9. An intramedullary fixation device as claimed in claim 8 and further including an elongated member of bio-compatible tubing having first and second ends and adapted to be affixed at said first end to said cylinder top cap.

10. An intramedullary fixation device as claimed in claim 9 wherein said second end of said elongated member has a metallic ring affixed thereto.

11. An intramedullary fixation device as claimed in claim 1 wherein said fixation means comprises a crossnail having a bore therethrough for receiving said cylinder member.

12. An intramedullary fixation device as claimed in claim 11 wherein said cross-nail comprises a blade portion and a bifurcated block portion through which said bore extends.

13. An intramedullary fixation device as claimed in claim 12 and further including a set screw adapted to draw the bifurcated portions of said block portion together.

14. An intramedullary device comprising;
    a nail portion and an adjustment assembly
    said nail portion having proximal and distal ends and means for attaching the distal end to the distal end of a patient's bone,
    a receptacle member having first and second bores therein forming an interior shoulder said receptacle member being affixed to the proximal end of said nail portion,
    said adjustment assembly comprising a hollow cylindrical member having proximal and distal ends,
    means within said hollow cylindrical member for adjusting the separation between said nail and said cylindrical member,
    and means for attaching said cylindrical member to the proximal end of the patient's bone.

15. An intramedullary device as claimed in claim 14 wherein said means for adjusting the separation comprises an adjustment shaft within said hollow cylindrical member, said shaft having proximal and distal ends, the distal end of said shaft being adapted to bear against said interior shoulder.

16. An intramedullary device as claimed in claim 15 and further including means for moving said adjustment shaft longitudinally within said hollow cylindrical member.

17. An intramedullary device as claimed in claim 16 wherein said hollow cylindrical member is threaded along the interior thereof and said means for moving comprises an adjustment screw.

18. An intramedullary device as claimed in claim 15 wherein said first bore of said receptacle member is splined and a portion of the interior of said hollow cylindrical member is splined, and said adjustment shaft has a plurality of splines on the exterior thereof, said splines on said shaft matching the splined interior of said hollow cylindrical member and the splined first bore of said receptacle.

19. An intramedullary device as claimed in claim 14 wherein said second bore of said receptacle member has a smaller diameter than said first bore and has internal threads extending longitudinally thereof.

20. An intramedullary device as claimed in claim 14 and further including a hollow end cap affixed to the proximal end of said hollow cylindrical member and an elongated bio-compatible tube affixed to said end cap.

21. The method of fixing and adjusting the separation between the separated portions of a long bone of a patient, wherein the separated long bone has a proximal end and a distal end, the proximal end of the bone having a neck and head portion, the method comprising the steps of drilling a hole through the head portion of the bone to the medullary canal inserting a nail member through the hole into the medullary canal and affixing the nail to the bone adjacent the distal end thereof inserting an adjustment assembly through the hole into the bone so that a movable portion of the adjustment assembly bears against the nail, fixing the adjustment assembly to the bone adjacent the proximal end thereof, and adjusting the separation between the nail member and the adjustment assembly by moving the moveable portion of the adjustment assembly.

22. The method as claimed in claim 21 in which the step of fixing the adjustment assembly to the bone comprises the steps of forming a notch in the head and neck of the proximal end of the bone prior to insertion of the nail member into the bone placing a cross-nail in the notch, and affixing the cross nail to the adjustment assembly after insertion thereof into the bone.

23. The method as claimed in claim 21 and further including the step of periodically inserting an adjusting tool through the hole in the bone to move the moveable portion of the adjustment assembly to vary the separation between the portions of the long bone.

* * * * *